United States Patent [19]

Leveque et al.

[11] 4,177,798

[45] Dec. 11, 1979

[54] APPARATUS FOR MEASURING THE MECHANICAL CHARACTERISTICS OF A MATERIAL SUCH AS LIVING SKIN

[75] Inventors: Jean-Luc Lèvêque, Montfermeil; Gilbert Gras, Aulnay Sous Bois, both of France

[73] Assignee: L'Oreal, Paris, France

[21] Appl. No.: 813,458

[22] Filed: Jul. 7, 1977

[30] Foreign Application Priority Data

Jul. 20, 1976 [FR] France .................. 76 22089

[51] Int. Cl.² .......................... A61B 5/10
[52] U.S. Cl. .......................... 128/774; 73/584; 73/575
[58] Field of Search ................ 128/2 S, 2 N, 2 R; 73/584, 575, 574, 655

[56] References Cited

U.S. PATENT DOCUMENTS

| | | | |
|---|---|---|---|
| 3,440,867 | 4/1969 | Prall et al. | 128/2 R X |
| 3,477,422 | 11/1969 | Jurist, Jr. et al. | 128/2 R |
| 3,734,082 | 5/1973 | Rawson et al. | 128/2 N |
| 4,064,870 | 12/1977 | Dumitrescu et al. | 128/2 N |

FOREIGN PATENT DOCUMENTS 1387854 3/1975 United Kingdom ............ 128/2 N

OTHER PUBLICATIONS

Bourne, "Measurement . . . Tendon Reflex", Med. and Biol. Eng., vol. 10, No. 5, pp. 692-696, 1972.

Primary Examiner—Lee S. Cohen
Attorney, Agent, or Firm—Brisebois & Kruger

[57] ABSTRACT

An apparatus for measuring mechanical characteristics of a material capable of transmitting vibration, particularly skin of a living subject. An impulse from a generator such as a small hammer causes a disturbance to propagate a wave along the material. A receiver includes a source of radiation and two photocells spaced apart and isolated from each other. The photocells receive the radiation after reflection from spaced locations on the surface of the material. The travel time of the propagated wave between the two reflection points is measured to determine the speed of wave propagation in the material.

15 Claims, 4 Drawing Figures

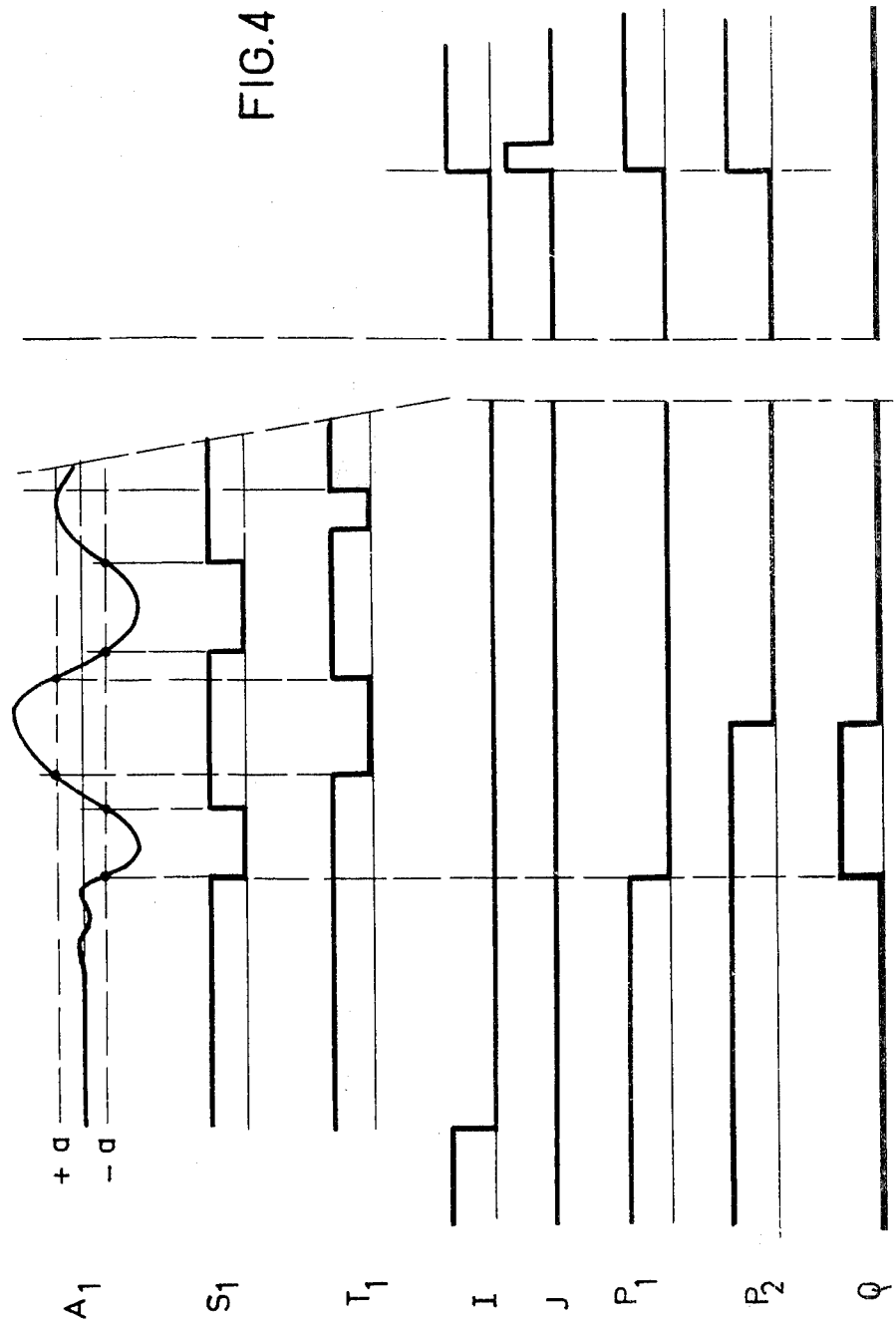

APPARATUS FOR MEASURING THE MECHANICAL CHARACTERISTICS OF A MATERIAL SUCH AS LIVING SKIN

SUMMARY OF THE INVENTION

In order to determine the nature of, or to verify the effect of certain skin treatments, specific skin characteristics are studied. The individual results of each test, as well as the overall relationship of the individual tests to each other over a period of time, are examined. One of the important characteristics of the skin is the volume of sebaceous secretion per unit surface. Several different types of measuring devices have already been suggested for studying this secretion characteristic. Another important characteristic of the skin is its elasticity which can be measured in order to determine the elastic modulus of the skin (Young's modulus).

To determine the elastic modulus of the skin of a living subject, presently existing devices can be used which study the speed of propagation of a mechanical wave between the emission point of the wave and a reception point spaced at a known distance from the emission point. Generally, a train of low amplitude, high frequency waves are generated on the specimen to be studied by a quartz oscillator. It is possible to study the propagation of this train of waves in the material under test in spite of the high frequency of the vibrations transmitted, as long as there is not too much dampening in the material. Unfortunately, in the case of skin, substantial difficulties are presented because the dampening coefficient is very high. In addition, the devices already known which use ultrasonics do not permit localized measurements on the surface of materials. The ultrasonics are propagated in the total body being studied and give rise to multiple reflections which must be interpreted. Therefore a surface measurement is not possible by the classical techniques.

On the contrary, the apparatus according to the present invention creates a mechanical disturbance on the surface of the material under test. The material is subjected to a short impulse which causes it to respond in a manner indicative of its dampening and frequency characteristics. The device for exciting the material does not impose its own working frequency on the material. Therefore because the generator itself does not impose on the material under test frequencies which are of no significance to the determination of properties of the material, the response effected is much richer in useful information and requires less processing.

In addition, in the known devices, the measurement of the propagation time of the train of waves in the specimens studied is not easily calculated in a single operation but requires several subtractions of time corresponding to the delay inherent in the wave generator circuit and in the receiver circuit. In these devices, the time measured is equal to the time of the propagation in the material studied, augmented by the difference between the time the clock begins to operate and the actual time the vibration is emitted onto the material. Also included in the time measured is the difference between the time of arrival of the vibration at the receiver and the time required to stop the clock. It is apparent then that added difficulties are introduced because in order to determine the time of propagation of the wave in the material being studied, it is necessary to subtract the delay times in the generator and the receiver.

Finally, another inconvenience of the presently known devices comes from the fact that in order to transmit vibrations in the materials studied it is necessary to physically apply the emitter or generator to the surface of the material to transmit the vibrations and also to apply the receiver on the specimen to detect the vibrations. However, in the case of measurements taken on the skin, it is to be noted that the skin is a living tissue and the application of such an emitter or a receiver on its surface modifies its local properties. For example, the loss of water by the skin is effected by the application of an emitter or receiver to the skin.

Therefore, it is evident that the existing devices which are based on the measuring of the propagation time of the wave between an emitter and a receiver are inappropriate for use as an effective means for measuring the modulus of elasticity of the skin.

An object of the present invention is to provide a means for determining the mechanical characteristics of the skin, in particular the elastic modulus of the skin, by studying the propagation of a disturbance brought about on the surface of the skin. The device according to the invention generates, in a first area of the skin, a disturbance such as a vibration which is propagated on the surface of the skin. The propagation is studied at a second area removed from the area directly disturbed. In addition, the device according to the invention registers the passage of a vibration in line with a point without engaging the skin with the receiver. Under these conditions it is evident that in the zone where the measurement is taken, the skin is not disturbed in any way and therefore its characteristics are kept perfectly constant during the test.

Finally, the apparatus according to the invention is capable of completely analyzing the disturbance which is propagated on the surface. The form, amplitude, and the characteristic frequency of the disturbance is generally provided and the entire signal received can be recorded on an appropriate rapid recording device. In a particular embodiment, if one is interested primarily in the time of propagation, the apparatus according to the invention detects the passage of vibrations at two points spaced apart from each other by a known distance. The processing circuits for each of two receivers, placed near the points are identical. Therefore the time measurement for the propagation of the vibration from the first receiver to the second receiver is not blemished with any error caused by different delay times in different electronic circuits.

It is apparent that the device according to the invention, which provides particularly interesting results in the case of measurements made on the skin of a living subject, can be used to measure mechanical characteristics of any material capable of transmitting a mechanical vibration. The study of vibrations permits determination of a number of characteristics of material under test, particularly the elastic modulus.

The present invention has then for its object an apparatus for measuring certain mechanical characteristics of a material susceptible of transmitting a vibration, especially the skin of a living subject. The device includes an emitter for generating a disturbance and a receiver separated from the emitter by a certain distance. The receiver comprises at least one source of light associated with two photo-sensitive receiving cells spaced one from the other. The light source or sources transmit radiation to the surface of the material being tested, and the photo-sensitive cells receive the radiation after reflection from the surface of the material under test.

In a preferred embodiment, the disturbance generated is a vibration. The disturbance can advantageously be a short impulse. The generator means for emitting the disturbance is a small hammer adapted for striking the surface of the material under test. The hammer strikes only one time for each test on the surface of the material. The striking force of the hammer is adjustable as a function of the material under test and the distance between the receiver and the emitter. The distance between the photo-sensitive receiving cells and the surface of the material studied is adjustable. The distance between the receiving cells and the material is adjusted such that the variation of light intensity received by each cell is essentially proportional to the variation of the distance between the receiving cell and the surface of the material which has been caused to vibrate by the generator. The light source or sources of the receiving means emit radiation only in one part of the spectrum, for example, a red radiation. Each photo-sensitive cell detects the passage of the first wave in its corresponding zone of reflection. This wave originates from the vibration which is propagated from the point on the material which has been struck by the hammer. An electronic channel controlled by the first receiving cell releases a time counter at the instant the first wave passes the first receiving cell. At the instant when the second receiving cell detects that the first wave is received in its zone of reflection, the counter is stopped. The two electronic channels associated with the two receiving cells are identical. Each channel includes two identical circuits connected to two inputs of an OR gate, one of the circuits permitting the indication of an increase in the distance of the material from the cell and the other circuit permitting the indication of a decrease of the distance. The time counter is released when a vibration passes the receiving cell only if the hammer has been previously activated to generate the vibrations. A manually controlled pushbutton activates the hammer to generate the vibrations. The counter is only activated during the period in which the user depresses the pushbutton. The release of the pushbutton causes a reset signal to be sent to two monostables, each of which receive in addition to the reset signal, a signal from one of the receiving cells. The output of these two monostables feeds the inputs of an Exclusive OR gate whose output in turn controls a clock associated with a registering device.

To better understand the object of the invention, an embodiment is given, purely as an example and non-limiting.

BRIEF DESCRIPTION OF THE DRAWINGS

FIG. 4 shows the wave forms at different points of the electronic circuit permitting the counting of the propagation time.

DETAILED DESCRIPTION OF THE PREFERRED EMBODIMENTS

Figure 1:
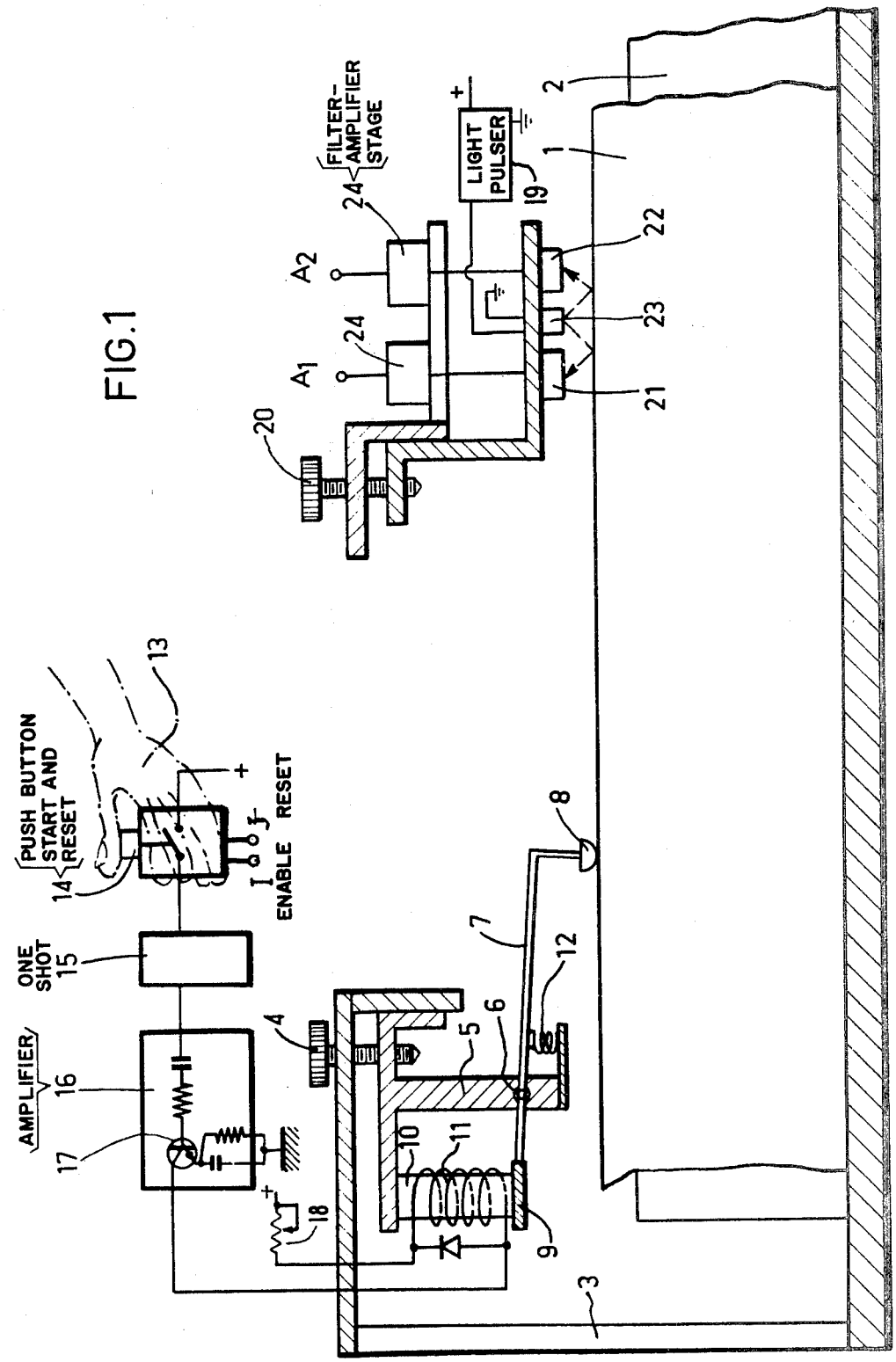
FIG. 1 shows schematically an apparatus according to the invention.

Referring to FIG. 1, an apparatus for measurement of the elastic modulus of the skin on an arm 1 of a living person is shown, and includes a splint or support 2 for supporting arm 1. The support 2 prevents any movement of the subject's arm during the measurement. The emitter for generating vibrations is spaced above support 2 and can be adjusted vertically relative to the material under test by turning a screw 4 so that slide unit 5 slides in relation to support 3. Slide 5 includes a pin 6 on which is pivoted, a rod 7 which includes at one extremity a striker or hammer 8 in the form of a hemisphere. At the other extremity of the rod 7 is a ferrite plate 9 facing an armature 10 of an electromagnet with a winding 11 activatable on command of the experimenter. Armature 10 is fixed to slide 5. Compression spring 12 acts on rod 7 to space plate 9 from armature 10 when winding 11 is unenergized.

The energization of winding 11 is controlled by the experimenter using a pushbutton 14 which permits closing a contact associated with a one-shot or monostable circuit 15. The monostable 15 controls amplifier stage 16 which includes a transistor 17 with its base connected to the monostable circuit 15. The transistor 17 is turned on at the moment when the pushbutton 14 is activated, thereby energizing the winding 11. A variable resistor or rheostat 18 can be connected in series between the collector of transistor 17 and winding 11 to provide for adjusting the extent of energization of the coil and correspondingly, the force with which hammer 8 strikes the material 1.

The receiver means according to the invention is fixed on a structure separate from the impulse generator to avoid all parasitic vibrations which could be transmitted by a common base. Adjustment of the distance between the receiving mechanism and the surface of the skin of arm 1 is controlled by adjusting screw 20.

The receiver includes two identical radiation-sensitive or photo-sensitive cells 21 and 22 which can be photo-transistors, and also includes a source of cold light, such as a light emitting diode 23. The light source 23 emits radiation of adjustable intensity which can be pulsed at a frequency as high as 1 MHz such as light pulser 19. In the case of a pulsed light of given intensity, a demodulator device can be connected between the cells and the rest of the processing circuitry. Source 23 emits a red light in the direction of arm 1. The light is reflected from the surface of the skin of the arm and is received at each of the two cells 21 and 22. Of course, it is possible to use several sources of light and, in particular, arrange them in such a way that the planes of reflection of the light are parallel to each other, and are perpendicular to a straight line passing through the hammer 8 in its position of striking and through the zones of reflection for the two receiving cells 21 and 22. Good results can be obtained by using a luminous source providing a beam of light with a mean luminous intensity on the order of 35 mcd and by placing the source and receiving cells 21 and 22 at a distance of above 4 mm from the surface of the skin to be studied. The intensity of the reflected light is, under these conditions, essentially proportional to the common distance adopted for the light source and for the receiving cells in relation to the skin to be studied, the coefficient of proportionality being important. The choice of this distance has a substantial influence on the sensitivity of the device.

Figure 2:
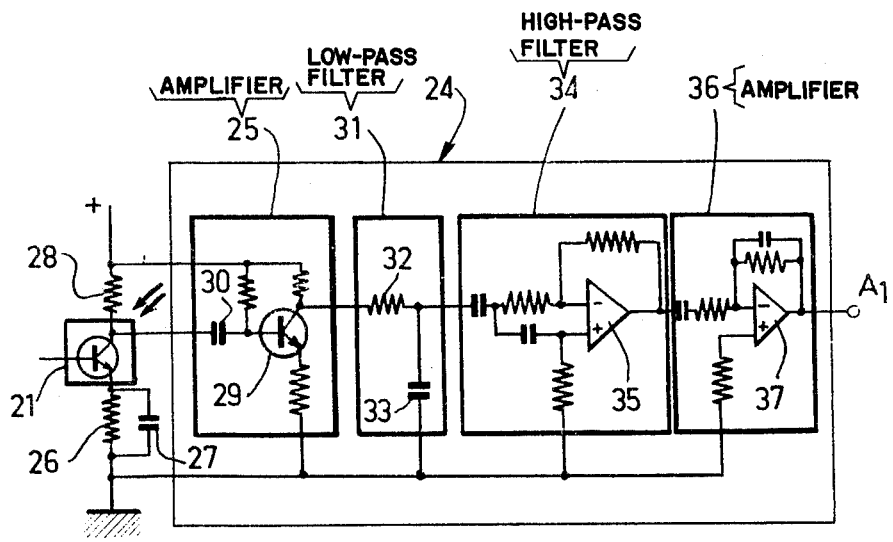
FIG. 2 shows schematically the first stage of the conversion circuit associated with each receiving cell.

Each of the cells 21 and 22 is associated with a first conversion stage circuit 24. Circuit 24 is shown in detail at FIG. 2 for the cell 21 in the case where the light source emits a continuous beam. The first conversion stage for cell 22 is identical to that shown for cell 21.

The collector of receiving cell photo-transistor 21 is connected to a first amplification stage 25. The emitter of photo-transistor 21 is connected by a resistor 26 and a capacitor 27 to ground. Positive bias is provided through resistor 28 to the collector of the photo-transistor 21. Amplifier 25 includes a transistor 29 with its base connected by a capacitor 30 to the collector of the cell 21.

The output of amplifier 25 is taken from the collector of transistor 29 which is connected to a low pass filter 31 which includes resistor 32 and condenser 33. This low pass filter attenuates all the frequencies above approximately 1 kHz. The output of filter 31 is connected to high pass filter 34 having operational amplifier 35. Filter 34 attenuates frequencies below 10Hz corresponding to what one considers as "biological noise" in the study of skin. The output of the operational amplifier 34 is connected to amplifier stage 36 which also includes an operational amplifier 37 connected in a conventional fashion. The amplifier stage 36 provides a gain of 10 between 10 Hz and 200 Hz.

The output of the first conversion stage 24 appears at output terminal $A_1$ (FIG. 3) for cell 21 and $A_2$ for the cell 22. When a wave caused by a striking blow of hammer 8 propagates in the direction of the receiver and arrives at the cell 21, this wave causes a modification of the distance between the skin and the cell 21 in the zone from which the light is reflected. A variation of the intensity of the light received by the photo-transistor 21 results. The signal received is processed in the first conversion stage 24 and a typical wave form that results is designated $A_1$ at FIG. 4.

In the device according to the invention, the linear relation existing between the distance of the cells from the surface of the material on the one hand and the luminous intensity received by the sensor or cells on the other hand permits visualization of the entire disturbance propagated along a straight line through the measuring zone, the visualization being in the form of electric signals.

The output obtained from conversion stage 24, represented by $A_1$ of FIG. 4, is an oscillating signal directly related to the mechanical disturbance on the surface. A similar signal appears at input $A_2$ of FIG. 3. The signal on $A_1$ and $A_2$ can then be directly recorded and processed by appropriate means to calculate all the desired data.

Figure 3:
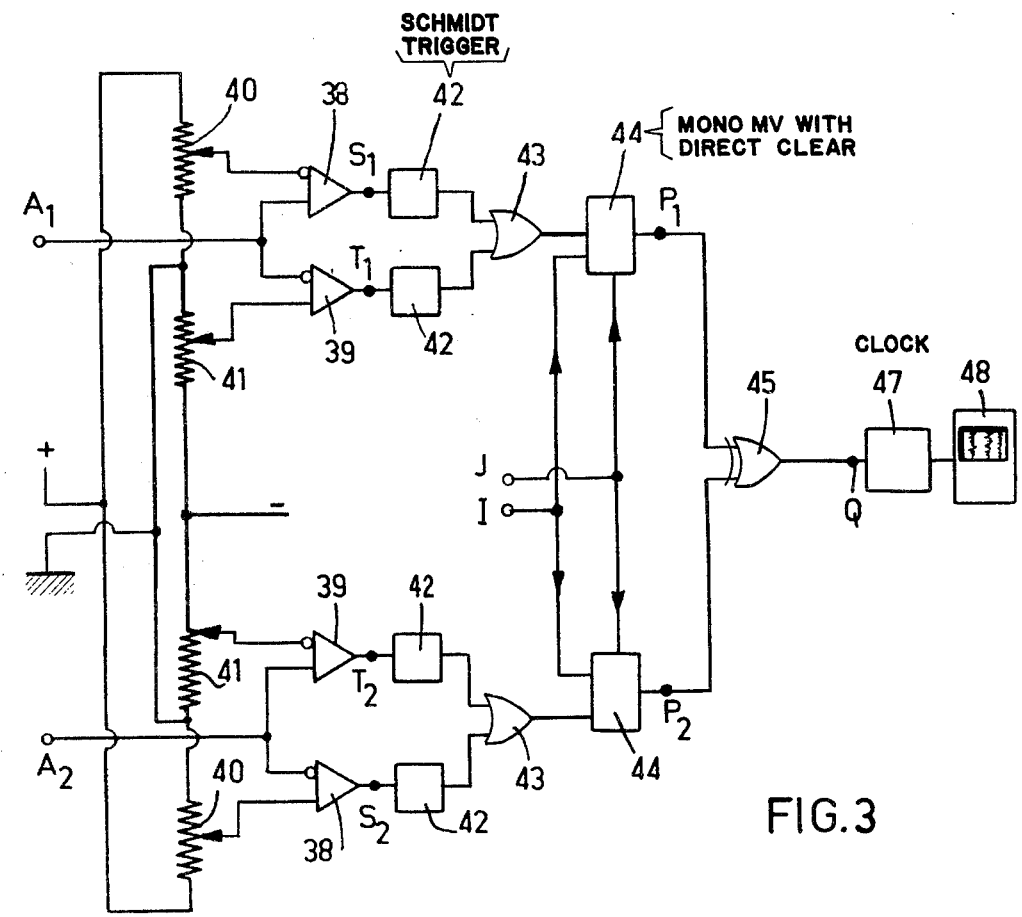
FIG. 3 is a schematic diagram of the two electronic channels each controlled by a receiving cell, the two channels in turn controlling a clock for permitting the counting of time.

However, in the particular mode of functioning where the preferred parameter is the speed of propagation, one can detect the arrival in the reflection zone of the first wave propagated. It is necessary to establish a threshold of sensibility corresponding to a variation below which one considers that there is no arrival of a wave. These thresholds are designated $(+a)$ and $(-a)$ on the first line of the graph of FIG. 4. The arrival of the first wave is registered by a decrease or an increase in the intensity of light received by the cell 21. As shown in FIG. 3 the signal obtained at point $A_1$ is sent to the inputs of two comparators 38 and 39. The other input of each comparator is connected to a source of voltage which is adjustable using potentiometers 40 and 41 respectively. The voltages are adjusted to correspond to the thresholds $(+a)$ and $(-a)$ mentioned above. The comparators 38 and 39 provide on their outputs $S_1$ and $T_1$ the signals which are shown on the second and third lines respectively of FIG. 4. The signal of $S_1$ is normally at the $+1$ level and changes to the zero level when the signal on $A_1$ is less than the threshold level $(-a)$. The signal at $T_1$ is normally at the $+1$ level and passes to the zero level when the signal on $A_1$ is greater than the threshold $(+a)$. The signal at the output $A_2$ is treated in like fashion and provides on terminals $S_2$ and $T_2$ signals analogous to those on terminals $S_1$ and $T_1$, with the difference being that the signals are not produced at the same time since the disturbance arrives at cell 22 a certain time after its arrival at cell 21.

The signals produced at $S_1$, $T_1$, $S_2$, and $T_2$ are transmitted to a Schmidt trigger circuit 42. The Schmidt trigger reverses the direction of variations of the signal. Thus, at the output from the trigger, the signal corresponding to $S_1$ passes from the zero level to the $+1$ level, and the signal corresponding to $T_1$ passes from the zero level to the $+1$ level. The two outputs corresponding to the terminal $S_1$ and $T_1$ are transmitted to the input of an OR gate 43. It is likewise for the signals corresponding to the terminals $S_2$ and $T_2$. The output of each of the OR gates 43 is sent to a monostable 44 which also receives the signal emitted from terminal I of the interruptor 14.

When the experimenter presses the pushbutton 14, the signal at input I goes from the $+1$ level to the zero level. When either one of the terminals $S_1$ or $T_1$ pass to the zero level, the output of the gate 43 goes to the $+1$ level. At the first time that the two inputs of monostable 44 are at the same level, the $+1$ level, the monostable 44 changes state and the output goes from the $+1$ level to the zero level. In the example which is represented on the first three lines of the graph of FIG. 4, one notes that the signal $P_1$, at the output of monostable 44 associated with the cell 21, changes state at the first leading descending edge of the signal at $S_1$. On the drawing of FIG. 4, the signals representing $S_2$ and $T_2$ are not shown, but the signal at $P_2$ is simply represented. The change of state of $P_2$ from the $+1$ level to the zero level is effected a certain time after the first transition has taken place on $P_1$ depending on the propagation time of the disturbance on the material. The return of the monostable 44 to its initial state is effected at the instant when the experimenter releases the pushbutton 14. The release of the button causes a signal on terminal J of the pushbutton, this signal returning the outputs $P_1$ and $P_2$ to the $+1$ level to reset the circuitry. Considering the short time lag existing between the leading descending edges of the signals $P_1$ and $P_2$ on the one hand, and the slowness of the finger of the experimenter on the pushbutton 14 on the other hand, the return to the initial state is always brought about well after the passage of the disturbance in front of the two cells 21 and 22.

The outputs of the two monostables 44 are transmitted to the two inputs of an Exclusive OR gate 45, whose output changes state from the zero level to the $+1$ level at the passage of the first descending edge, that is to say that of $P_1$, and which returns to the zero level at the passage of the second descending edge, that is to say of $P_2$. The signal at the output Q is shown at the last line of FIG. 4. This signal controls a clock 47, which counts the time during the total duration of the positive output of signal Q. The counting of the clock 47 is posted on a visualization device or chart type recorder 48. One is able to obtain the measure of time in micro-seconds of the propagation of the wave of the vibration generated by the impulse of the hammer 8 on the skin, between the reflection zone for the cell 21 and the zone for the cell 22. One has verified that the measures effected are perfectly reproducible.

It is clear that the apparatus according to the invention permits the measurement of mechanical characteristics of the skin without the skin being disturbed by contact of the device to the zone of the skin to be measured. The receiver cells are not applied on the skin and, in addition, the propagation time given by the device 48 does not entail errors since the calculation is brought about from information coming from two identical circuits connected in parallel.

It is understood that the above embodiment in no way is limiting and may be modified without going beyond the spirit of the invention. In particular, it is possible to study with the device, the mechanical characteristics of the material other than the Young's modulus. For example, it is possible to calibrate the passage of two successive maxima in the wave train or to study the evolution of the amplitude of the wave of the wave train. It would be sufficient in this case to modify the electronic circuit associated with the receiver cells to obtain a measure of the characteristic deemed of interest.

What is claimed is:

1. Apparatus for measuring certain mechanical characteristics of a material capable of transmitting a vibration, and which can be the skin of a living subject, said apparatus comprising, emitter means for generating a disturbance in the material, and receiver means spaced from said emitter means by a certain distance, the receiver means comprising at least one luminous source associated with two photosensitive receiving cells isolated one from the other, characterized by the fact that the luminous source sends radiation to the surface of the material under test, the photocells receiving the said radiation after reflection from the surface of the material under test, and circuit means connected to said photocells for registering characteristics of said material in response to the reflected radiation received by said photocells.

2. Apparatus according to claim 1, wherein the disturbance generated by the emitter means is a vibration.

3. Apparatus according to claim 1, wherein the disturbance generated by the emitter means is a short impulse.

4. Apparatus according to claim 3, wherein the emitter means comprises a small hammer for striking the surface of the material under test to generate the short impulse.

5. Apparatus according to claim 4, further comprising means to cause the hammer to strike the surface of the material a single time during each test of the material.

6. Apparatus according to claim 4, further comprising means for adjusting the striking force of the hammer.

7. Apparatus according to claim 4, wherein each photocell registers the passage of a first wave in its reflection zone, this wave emanating from the point of impact of the material which has been struck by the hammer, a time counter, electronic channel means controlled by the first cell for starting said time counter at the instant of detection of the first wave by the first cell, and electronic channel means controlled by the second cell for stopping said counter at the instant of detection of the wave by the second cell.

8. Apparatus according to claim 7, wherein each electronic channel means comprises an identical channel.

9. Apparatus according to claim 7, wherein each electronic channel means comprises, an OR gate, and two identical circuits connected between an output of a cell and the respective inputs of said OR gate, one of these circuits registering an increase in the distance between the material under test and the receiving cell and the other circuit registering a decrease of the said distance.

10. Apparatus according to claim 7, further comprising means for starting the time counter by the passage of a vibration in front of the first cell only when the hammer is operated to generate the vibration.

11. Apparatus according to claim 10, further comprising manually controllable pushbutton means for operating the hammer, means for enabling said counter during the whole period during which the pushbutton means is applied, means responsive to the release of the pushbutton means for creating a signal for returning the apparatus to its initial state, and comprising two monostables each responsive to signals from the pushbutton means and from one of the electronic channel means, and means responsive to the outputs of the monostables for controlling the time counter and comprising an Exclusive OR gate having its inputs connected to the outputs of the monostables, and its output controlling the time counter.

12. Apparatus according to claim 1, further comprising means for adjusting the distance between the photosensitive receiving cells and the surface of the material.

13. Apparatus according to claim 12, wherein the means for adjusting the distance between receiving cells and the material under study comprises selectively adjustable means for adjusting the distance so that the variation of the intensity of the light received by each cell is appreciably proportional to the variation of the distance between the receiving cell and the surface of the material when disturbed.

14. Apparatus according to claim 1 wherein the luminous source of the receiver means emits radiation in solely one part of the light spectrum.

15. Apparatus according to claim 1, further comprising means for pulsing the luminous source of the receiver means to emit a pulsed radiation with a frequency of pulsation between zero and 1 MhZ.

* * * * *